United States Patent
Miążek et al.

(10) Patent No.: US 11,274,161 B2
(45) Date of Patent: Mar. 15, 2022

(54) MONOCLONAL ANTIBODIES THAT SPECIFICALLY RECOGNIZE CANINE DLA-DR ANTIGEN AND THEIR USES

(71) Applicant: Instytut Immunologii i Terapii Doświadczanej Polskiej Akademii Nauk, Wroclaw (PL)

(72) Inventors: Arkadiusz Miążek, Pegow (PL); Marta Lisowska, Wroclaw (PL); Andrzej Rapak, Brzeg (PL)

(73) Assignee: Instytut Immunologii i Terapii Doświadczanej Polskiej Akademii Nauk, Wroclaw (PL)

( * ) Notice: Subject to any disclaimer, the term of this patent is extended or adjusted under 35 U.S.C. 154(b) by 79 days.

(21) Appl. No.: 16/076,801

(22) PCT Filed: Mar. 2, 2017

(86) PCT No.: PCT/PL2017/050014
§ 371 (c)(1),
(2) Date: Aug. 9, 2018

(87) PCT Pub. No.: WO2017/151000
PCT Pub. Date: Sep. 8, 2017

(65) Prior Publication Data
US 2019/0144560 A1 May 16, 2019

(30) Foreign Application Priority Data
Mar. 2, 2016 (PL) .......................... 416359

(51) Int. Cl.
*C07K 16/30* (2006.01)
*C07K 16/28* (2006.01)
*G01N 33/574* (2006.01)

(52) U.S. Cl.
CPC ...... *C07K 16/3061* (2013.01); *C07K 16/2833* (2013.01); *C07K 16/30* (2013.01); *G01N 33/57407* (2013.01); *G01N 33/57426* (2013.01); *C07K 2317/24* (2013.01); *C07K 2317/734* (2013.01)

(58) Field of Classification Search
CPC . C07K 16/3061; C07K 16/2833; C07K 16/30
USPC ........................................ 424/174.1
See application file for complete search history.

(56) References Cited

U.S. PATENT DOCUMENTS 9,079,949 B1    7/2015    Andrien, Jr. et al.

FOREIGN PATENT DOCUMENTS

| CN | 102690789 | 9/2012 |
|---|---|---|
| EP | 0289053 | 11/1988 |
| EP | 2949672 | 12/2015 |
| WO | WO 2014/114801 | 7/2014 |
| WO | WO 2014111704 | 7/2014 |

OTHER PUBLICATIONS

MacCallum et al. (J. Mol. Biol. (1996) 262:732-745).*
De Pascalis et al. The Journal of Immunology (2002) 169, 3076-3084.*
Casset et al. ((2003) BBRC 307, 198-205).*
Vajdos et al. ((2002) J. Mol. Biol. 320, 415-428).*
Holm et al. ((2007) Mol. Immunol. 44: 1075-1084).*
Chen et al. J. Mol. Bio. (1999) 293, 865-881.*
Wu et al. (J. Mol. Biol. (1999) 294, 151-162).*
Ward et al. (Nature 341:544-546 (1989)).*
Lisowska et al (Hematol Oncol. Mar. 24, 2018 36(3): 554-560 (abstract only)).*
Lisowska etal (Cancers (Basel). Oct. 2019; 11(10): 1438).*
Steplewski et al., Canine lymphoma-associated antigens defined by murine monoclonal antibodies; Cancer Immunol. Immunother. 24:197-201 (1987).
Sarmiento et al., A canine lymphocyte surface antigen detectable by a monoclonal antibody (DT200); Canadian J. Vet. Res. 51:110-116 (1987).

* cited by examiner

*Primary Examiner* — Lynn A Bristol
(74) *Attorney, Agent, or Firm* — Grimes & Yvon LLP

(57) ABSTRACT

Disclosed are monoclonal antibodies and their fragments that specifically recognize canine DLA-DR antigen and their use in the treatment, prevention, or diagnosis of leukemias and lymphomas, especially canine.

6 Claims, 7 Drawing Sheets
Specification includes a Sequence Listing.

Sequences of murine immunoglobulin B5 variable regions

B5VH:
CAGGTCCAACTGCAACAGTCTGGACCTGAACTGATGAAGCCTGGGACTTCAGTGAAGATTTCCTGCAA
GGCTTCTGGCTACACTTTCACAAGCTACTTTATACACTGGATGAAGCAGAGGCCTGGACAGGGACTTG
AGTGGATTGGATGGATTTTTCCTGGAAATATTAATGCTAAATATAATGAGAACTTCAGGGGCAAGGCC
ACACTGACGGCAGACACATCCTCCACCACCGCCTACATACAGCTCAGCAGCCTAACATCTGAGGACTC
TGCGGTCTATTACTGTGCAAGAGCCCCTTTACTGGGGAACTACTTTGACTACTGGGGCCAAGGCACCA
CTCTCACAGTCTCCTCA (SEQ ID NO: 17)

```
Q V Q L Q Q S G P E L M K P G T S V K I S C K A S G Y T F T S Y F I H W M K
1                   10                  20                  30  CDR-1

Q R P G Q G L E W I G W I F P G N I N A K Y N E N F R G K A T L T A D T S S
    40               50    52 a       CDR-2 60                  70

T T A Y I Q L S S L T S E D S A V Y Y C A R A P L L G N Y F D Y W G Q T T
        80  82 a b c              90          CDR-3    100a b

L T V S S  (SEQ ID NO: 7)
 110
```

B5Vk:
GAGCTCGTGCTCACCCAGTCTCCAGCTTCACTGTCTGCATCTGTGGGAGAAACTGTCACCATCACATG
TGGAGCAAGTGAGAATATTTACGGTGCTTTAAGTTGGTATCAGCGGAAACAGGGCAAGTCTCCTCAGC
TCCTGATCTATGGTGCAACCAACTTGGCAGATGGCTTGTCATCGAGGTTCAGTGGCAGTGGATCTGGT
AGACAGTATTCTCTCAAGATCAGTAGCCTGCATCCTGACGATGTTGCAACGTATTACTGTCAAAATTT
TTTTATTACTCCGTACACGTTCGGAGGGGGGACCAAGCTGGAAATGAAACGG (SEQ ID NO: 18)

```
E L V L T Q S P A S L S A S V G E T V T I T C G A S E N I Y G A L S W Y Q R
1                   10                  20          CDR-1     30

K Q G K S P Q L L I Y G A T N L A D G L S S R F S G S G S G R Q Y S L K I S
    40               50  CDR-2         60                      70

S L H P D D V A T Y Y C Q N F F I T P Y T F G G G T K L E M K R
        80              90   CDR-3      100
(SEQ ID NO: 15)
```

FIG. 1

Sequences of murine immunoglobulin E11 variable regions

E11VH:
CAGGTCCAGCTGCAGCAGTCTGGACCTGAACTGGTGAAGCCTGGGACTTCAGTGAAGATATCCTGCAA
GGCTTCTGGCTACAGGTTCACAAGCTACTATATACACTGGGTGAAGCAGAGGCCTGGACAGGGACTTG
AGTGGATTGGATGGATTTATCCTGGAAGTGGCAATAGTAAGTACAATGAAGTTCAAGGGCAAGGCC
ACACTGACGGCAGACACATCCTCCAGCACTGCCTACATGCAGCTCAGCAGCCTAACATCTGAGGACTC
TGCGGTCTTTTACTGTGCAAGAGGTGGCTCAGGCTACGTAGGGGCTATGAACTGCTGGGGTCAAGGAA
CCTCAGTCACCGTCTCCTCA (SEQ ID NO: 19)

Q V Q L Q Q S G P E L V K P G T S V K I S C K A S G Y R F T S Y Y I H W V K
1           10                     20                   30   CDR-1

Q R P G Q G L E W I G W I Y P G S G N S K Y N E K F K G K A T L T A D T S S
  40                 50   52 a    CDR-2   60                   70

S T A Y M Q L S S L T S E D S A V F Y C A R G G S G Y V G A M N C W G Q G T
    80   82 a b c              90       CDR-3   100a b c

S V T V S S (SEQ ID NO: 8)
  110

E11Vk:
GACATCCAGATGACTCAGTCTCCAGCCTCCCTATCTGCATCTGTGGGAGAAACTGTCACCATCACATG
TCGAACAAGTGAGAATATTTACAGTTTTTTAGCATGGTCTCAGCAGAAACAGGGAAAATCTCCTCAGC
TCCTGGTCTATAATGCAAAAACCTTAGTAGAAGGTGTGCCATCAAGGTTCAGTGGCAGTGGATCAGGC
ACACAGTTTTCTCTGAGGATCAACAGCCTGCAGCCTGAAGATTTTGGGAGTTATTACTGTCAACATCA
TTATGGTACTCCTCTCACGTTCGGCGCTGGGACCAAGCTGGAGGTGAAACGG (SEQ ID NO: 20)

D I Q M T Q S P A S L S A S V G E T V T I T C R T S E N I Y S F L A W S Q Q
1          10                    20        CDR-1   30

K Q G K S P Q L L V Y N A K T L V E G V P S R F S G S G S G T Q F S L R I N
  40                50 CDR-2          60                  70

S L Q P E D F G S Y Y C Q H H Y G T P L T F G A G T K L E V K R
   80               90   CDR-3
(SEQ ID NO: 16)

FIG. 2

FACS analysis of canine and human cell lines with B5 and E11 antibodies

Reactivity of B5 and E11 antibodies to HEK293 cells transfected with gene constructs coding for DLA-DR chains by a) FACS and b) Western blotting
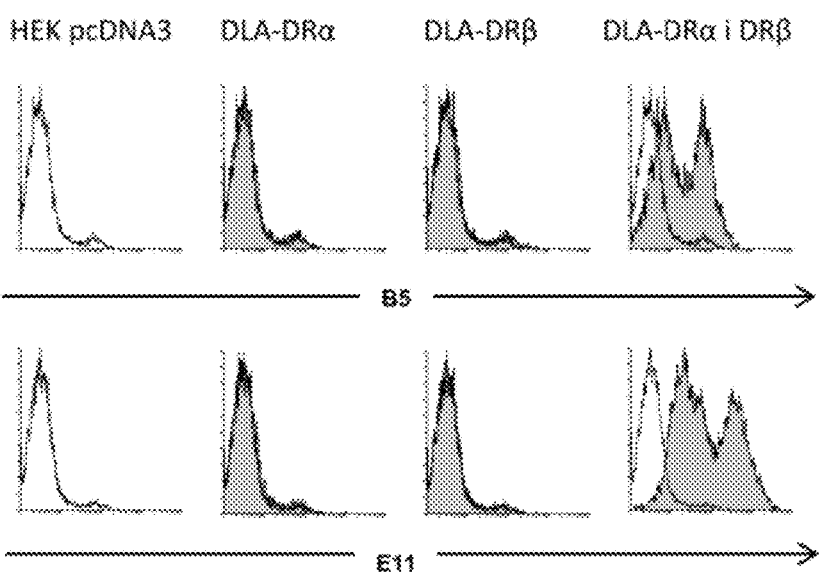
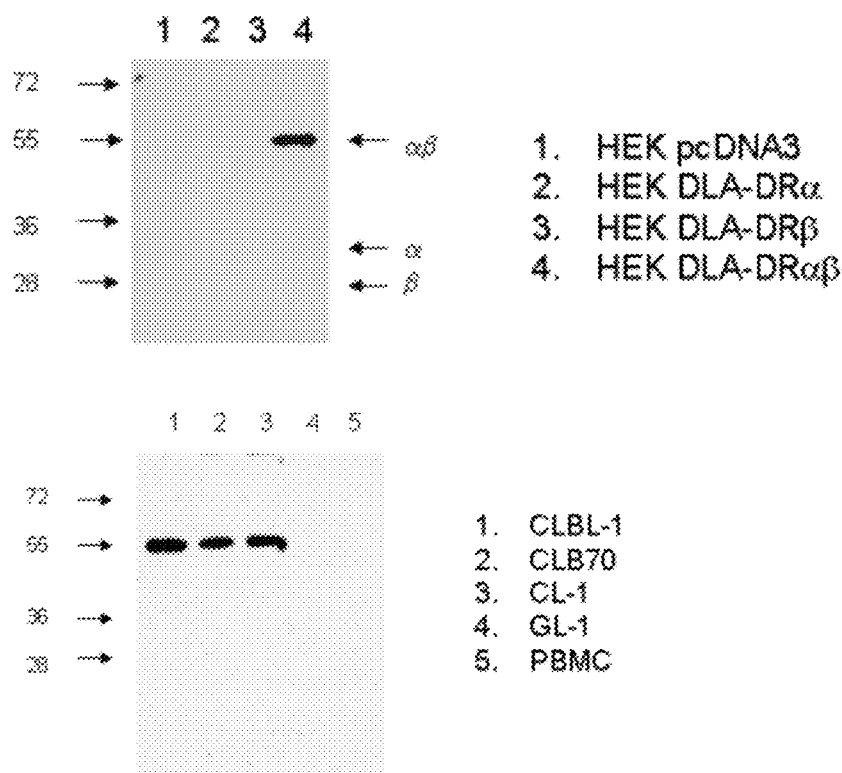

cE11

Heavy chain

ATGGGATGGAGCTGGATCTTTCTCTTCCTCCTGTCAGGAACTGCAGGTGTCCATTGCCAGGTCCAGCTGCAGCAG
TCTGGACCTGAACTGGTGAAGCCTGGGACTTCAGTGAAGATATCCTGCAAGGCTTCTGGCTACAGGTTCACAAGC
TACTATATACACTGGGTGAAGCAGAGGCCTGGACAGGGACTTGAGTGGATTGGATGGATTTATCCTGGAAGTGGC
AATAGTAAGTACAATGAGAAGTTCAAGGGCAAGGCCACACTGACGGCAGACACATCCTCCAGCACTGCCTACATG
CAGCTCAGCAGCCTAACATCTGAGGACTCTGCGGTCTTTTACTGTGCAAGAGGTGGCTCAGGCTACGTAGGGGCT
ATGAACTGCTGGGGTCAAGGAACCTCAGTCACCGTCTCCTCAGCCTCCACCACGGCCCCCTCGGTTTT
TCCCACTGGCCCCAGCTGCGGGTCCACTTCCGGCTCCACGGTGGCCCTGGCCTGCCTGGTGTCAGGCTACTTCC
CCGAGCCTGTAACTGTGTCCTGGAATTCCGGCTCCTTGACCAGCGGTGTGCACACCTTCCCGTCCGTCCTGCAGT
CCTCAGGGCTCTACTCCCTCAGCAGCATGGTGACAGTGCCCTCCAGCAGGTGGCCCAGCGAGACCTTCACCTGCA
ACGTGGCCCACCGGCCAGCAAAACTAAAGTAGACAAGCCAGTGCCCAAAAGAGAAAATGGAAGAGTTCCTCGCC
CACCTGATTGTCCCAAATGCCCAGCCCTGAAATGCTGGGAGGGCCTTCGGTCTTCATCTTTCCCCGAA
ACCCAAGGACACCCTCTTGATTGCCCGAACACCTGAGGTCACATGTGTGGTGGTGGATCTGGACCCAGAA
GACCCTGAGGTGCAGATCAGCTGGTTCGTGGACGGTAAGCAGATGCAAACAGCCAAGACTCAGCCTCGTG
AGGAGCAGTTCAATGGCACCTACCGTGTGGTCAGTGTCCTCCCCATTGGGCACCAGGACTGGCTCAAGGG
GAAGCAGTTCACGTGCAAAGTCAACAACAAAGCCCTCCCATCCCCGATCGAGAGGACCATCTCCAAGGCC
AGAGGGCAAGCCCATCAGCCCAGTGTGTATGTCCTGCCGCCATCCCGGGAGGAGTTGAGCAAGAACACAG
TCAGCTTGACATGCCTGATCAAAGACTTCTTCCCACCTGACATTGATGTGGAGTGGCAGAGCAATGGACA
GCAGGAGCCTGAGAGCAAGTACCGCACGACCCCGCCCAGCTGGACGAGGACGGGTCCTACTTCCTGTAC
AGCAAGCTCTCTGTGGACAAGAGCCGCTGGCAGCGGGGAGACACCTTCATATGTGCGGTGATGCATGAAG
CTCTACACAACCACTACACACAGGAATCCCTCTCCCATTCTCCGGGTAAATGA (SEQ ID NO: 35)

```
M G W S W I F L F L L S G T A G V H C Q V Q L Q Q S G P E L V K P G T S V K
I S C K A S G Y R F T S Y Y I H W V K Q R P G Q G L E W I G W I Y P G S G N
S K Y N E K F K G K A T L T A D T S S S T A Y M Q L S S L T S E D S A V F Y
C A R G G S G Y V G A M N C W G Q G T S V T V S S A S T T A P S V F P L A P
S C G S T S G S T V A L A C L V S G Y F P E P V T V S W N S G S L T S G V H
T F P S V L Q S S G L Y S L S S M V T V P S S R W P S E T F T C N V A H P A
S K T K V D K P V P K R E N G R V P R P P D C P K C P A P E M L G G P S V F
I F P P K P K D T L L I A R T P E V T C V V V D L D P E D P E V Q I S W F V
D G K Q M Q T A K T Q P R E E Q F N G T Y R V V S V L P I G H Q D W L K G K
Q F T C K V N N K A L P S P I E R T I S K A R G Q A H Q P S V Y V L P P S R
E E L S K N T V S L T C L I K D F F P P D I D V E W Q S N G Q Q E P E S K Y
R T T P P Q L D E D G S Y F L Y S K L S V D K S R W Q R G D T F I C A V M H
E A L H N H Y T Q E S L S H S P G K Stop (SEQ ID NO: 37)
```

Light chain

ATGAGTGTGCCCACTCAGGTCCTGGGGTTGCTGCTGCTGTGGCTTACAGGTGCCAGATGTGACATCCAGATGACT
CAGTCTCCAGCCTCCCTATCTGCATCTGTGGGAGAAACTGTCACCATCACATGTCGAACAAGTGAGAATATTTAC
AGTTTTTTAGCATGGTCTCAGCAGAAACAGGGAAAATCTCCTCAGCTCCTGGTCTATAATGCAAAAACCTTAGTA
GAAGGTGTGCCATCAAGGTTCAGTGGCAGTGGATCAGGCACACAGTTTTCTCTGAGGATCAACAGCCTGCAGCCT
GAAGATTTTGGGAGTTATTACTGTCAACATCATTATGGTACTCCTCTCACGTTCGGCGCTGGGACCAAGCTGGAG
GTGAAACGGGCTGATGCTGCACCAACTGTATCCTTGTTCCAACCATCTCCAGACCAGTTACACACAG
GAAGTGCCTCTGTTGTGTGTTTGCTGAATAGCTTCTACCCCAAAGACATCAATGTCAAGTGGAAAGTGGATGGTG
TCATCCAAGACACAGGCATCCAGGAAAGTGTCACAGAGCAGGACAAGGACAGTACCTACAGCCTCAGCAGCACCC
TGACGATGTCCAGTACTGAGTACCTAAGTCATGAGTTGTACTCCTGTGAGATCACTCACAAGAGCCTGCCCT
CCACCCTCATCAAGAGCTTCCAAAGGA<u>GCGAGTGTCAGAGAGTGGACTAA</u> (SEQ ID NO: 36)

```
M S V P T Q V L G L L L L W L T G A R C D I Q M T Q S P A S L S A S V G E T
V T I T C R T S E N I Y S F L A W S Q Q K Q G K S P Q L L V Y N A K T L V E
G V P S R F S G S G S G T Q F S L R I N S L Q P E D F G S Y Y C Q H H Y G T
P L T F G A G T K L E V K R A D A A P T V S L F Q P S P D Q L H T G S A S V
V C L L N S F Y P K D I N V K W K V D G V I Q D T G I Q E S V T E Q D K D S
T Y S L S S T L T M S S T E Y L S H E L Y S C E I T H K S L P S T L I K S F
Q R S E C Q R V D Stop (SEQ ID NO: 38)
```

FIG. 6

Reactivity of chimeric murine-canine cE11 antibodies with canine and human lymphoma lines CH89 (dog NK)

CLBL1 (dog B-cell)

HUT-78 (human T-cell)

MONOCLONAL ANTIBODIES THAT SPECIFICALLY RECOGNIZE CANINE DLA-DR ANTIGEN AND THEIR USES

CROSS-REFERENCE TO RELATED APPLICATIONS

This application is the National Stage of International Application No. PCT/PL2017/050014, filed on Mar. 2, 2017, and claims the benefit of priority to PL Application No. P.416359, filed on Mar. 2, 2016, both of which are hereby incorporated by reference in their entireties for all purposes.

SEQUENCE LISTING

The instant application contains a Sequence Listing which has been filed electronically in ASCII format and is hereby incorporated by reference in its entirety. Said ASCII copy, created on Jan. 31, 2019, is named JWP_001_US1_SL.txt and is 28,200 bytes in size.

BACKGROUND AND SUMMARY

The invention relates to monoclonal antibodies, and fragments thereof, which specifically recognize canine DLA-DR antigen and their use in the treatment, prevention or diagnosis of leukemias and lymphomas, especially canine.

Lymphoid diseases (leukemia, lymphoma) in dogs account for about 30% of all diagnosed types of cancer in this animal species. The most common are B-cell non-Hodgkin lymphomas, equivalent to human non-Hodgkin lymphomas (NHL), which account for about 20% of all canine tumors and about 85% of lymphoid tumors. The incidence of lymphomas in the dog population is higher than in humans. Dogs of different races and ages are affected, but the largest group of patients are dogs aged about 10 years.

Traditional treatment regimens for human lymphomas are used, based on classical cytostatic drugs (doxorubicin, vincristine, prednisolone, etoposide) administered alone or in combination. A disadvantage of such a therapy is small specificity with large undesirable effects. A more comprehensive therapy offers faster recovery and longer survival time, but this procedure is more costly and more toxic. In turn, chemotherapy with single drugs is cheaper but less effective. Despite the initial remission of the disease, conventional chemotherapy results in resistance development and relapse. A serious problem is the financial cost that must be borne by the dog owner. At the moment there are no other effective treatment methods that at the same time are mild and affordable. Due to the anatomical and physiological similarities, dogs have become a useful research model in development of drugs and treatments for humans.

Also naturally occurring cancers in dogs show a number of common features.

Humanized monoclonal antibodies recognizing CD20 antigen on lymphoid B cells (Rituximab, Ofatumumab) or CD33 antigen on myeloid cells (Gemtuzumab), B and T cells (CD52) (Alemtuzumab) are used to treat human lymphomas and leukemias. The disadvantage of these antibodies is that they affect normal lymphoid cells, but the natural process of renewal circulating B cells from the bone marrow prevents permanent immune deficiencies associated with deletion of these cells by the anti-CD20 immunotherapy. Attempts to use Rituximab in dogs were unsuccessful due to the lack of cross-reactivity with canine CD20. Novel monoclonal antibodies that specifically recognize the canine CD20 were obtained by Rue S. M. el al. and tested in the context of treatment canine B-cell lymphoma (Sarah M. Rue, Brendan P. Eckelman, Jem A. Efe, Kristin Bloink, Quinn L. Deveraux, David Lowery, Marc Nasoff, Veterinary Immunology and Immunopathology 164 (2015) 148-159).

In addition to the CD20 and CD33 antigens, the HLA-DR antigen, which belongs to the main histocompatibility complex MHC II, is considered as a target for anticancer therapy. Its expression is significantly increased in B-cell leukemias and lymphomas and in a number of autoimmune diseases, including rheumatoid arthritis (Malone D G, Wahl S M, Tsokos M, Cattell H, Decker J L, Wilder R L., J Clin Invest. 1984 October; 74(4):1173-85) and multiple sclerosis (Olerup O, Fredrikson S, Olsson T, Kam-Hansen S. Lancet, 1987 Aug. 8; 2(8554):327).

Currently, human clinical trials are underway for humanized antibody against alpha subunit of human HLA-DR (hL243) (Goldenberg et al., U.S. Pat. No. 8,992,917B2). HLA-DR antigen is released from the cell surface by proteolytic digestion and is detectable in serum and other body fluids. Determination of the soluble form (s-HLA-DR) may be an important diagnostic marker for lymphoproliferative and autoimmune diseases, and blocking the interaction of s-HLA-DR with Tirc7 receptors on the surface of CD4+ T cells may affect their activation (Frischer J, Reindl M, Künz B, Berger T, Schmidt S, Milford E, Knosp E, Lassmann H, Utek N. Mult Scler. 2014 Feb. 13).

Sarmiento and Valli have described a monoclonal antibody recognizing T200 antigen (LCA, CD45) that may be used in immunohistochemistry for detection of canine lymphoid tumor cells (Sarmiento U M, Valli V. A canine Lymphocyte Surface Antigen detectable by a Monoclonal antibody (DT200). Can J Vet Res 1987, 51, 110-116).

Steplewski and co-workers have described several monoclonal antibodies obtained against canine lymphoma cells and recognizing unidentified surface antigens on canine lymphoid cells. These antibodies reacted to varying degrees with normal lymphoid cells (Z. Steplewski, K. A. Jeglum, C. Rosales, N. Weintraub. Canine lymphoma-associated antigens defined by murine monoclonal antibodies. Cancer Immunol. Immunother. 1987, 24, 197-201; CA1340898 "Monoclonal Antibodies Against Lymphoma-associated Antigens, Hybrid Cell Lines Producing These Antibodies, and Use Therefore").

The object of the invention is to provide new substances suitable for the treatment, prevention and diagnosis of leukemias and lymphomas in dogs.

Surprisingly, the problem described above is solved in the present invention.

The subject of the invention is a polypeptide that is a heavy chain variable region of an antibody specifically interacting with canine lymphoma and leukemia cells, comprising CDR region having a sequence selected from SEQ ID Nos. 1-6, preferably comprising CDR regions designated as SEQ ID Nos. 1-3 or comprising CDR regions designated as SEQ ID Nos. 4-6, especially having the amino acid sequence designated as SEQ ID No. 7 or 8.

A further subject of the invention is a polypeptide that is a light chain variable region of an antibody specifically interacting with canine lymphoma and leukemia cells, comprising CDR region having a sequence selected from SEQ ID Nos. 9-14, preferably comprising CDR regions designated as SEQ ID Nos. 9-11 or containing CDR regions designated as SEQ ID Nos. 12-14, especially having the amino acid sequence designated as SEQ ID No. 15 or 16.

The polypeptides of the invention as defined above may be used to obtain antibodies recognizing specifically the canine DLA-DR antigen, preferably suitable for the treatment, prevention or diagnosis of leukemias and lymphomas, especially canine.

A further subject of the invention is an antibody specifically interacting with canine lymphoma and leukemia cells having:

A) antibody heavy chain containing CDR regions designated as SEQ ID Nos. 1-3, especially comprising heavy chain variable region having an amino acid sequence designated as SEQ ID No. 7 and
antibody light chain containing CDR regions designated as SEQ ID Nos. 9-11, especially comprising light chain variable region having an amino acid sequence designated as SEQ ID No. 15
or
B) antibody heavy chain containing CDR regions designated as SEQ ID Nos. 4-6, especially comprising heavy chain variable region having an amino acid sequence designated as SEQ ID No. 8 and
antibody light chain containing CDR regions designated as SEQ ID Nos. 12-14, especially comprising light chain variable region having an amino acid sequence designated as SEQ ID No. 16.

Preferably, the antibody of the invention is a chimeric murine-canine antibody having: antibody heavy chain containing heavy chain constant region derived from a canine immunoglobulin, especially from a canine antibody, and antibody light chain containing light chain constant region derived from a canine immunoglobulin, especially from a canine antibody. An example of such a chimeric caninized antibody is the cE11 antibody described in Example 7. In an analogous manner, a caninized antibody containing CDR regions derived from B5 antibody can be obtained from polypeptides disclosed in the application.

Preferably, the antibody of the invention is an antibody produced by a hybridoma selected from cell lines deposited in DSM under access numbers DSM ACC3287 and DSM ACC3288.

A further subject of the invention is an antibody as defined above for use in the treatment or prevention of leukemia, especially canine, or lymphoma, especially canine.

A further subject of the invention is an antibody as defined above for use in the diagnosis of leukemia, especially canine, or lymphoma, especially canine.

A further subject of the invention is a hybridoma selected from cell lines deposited in DSM under access numbers DSM ACC3287 and DSM ACC3288.

BRIEF DESCRIPTION OF THE DRAWINGS

FIG. 1 shows nucleotide and amino acid sequences of the murine immunoglobulin B5 variable regions.

FIG. 2 shows nucleotide and amino acid sequences of the murine immunoglobulin E11 variable regions.

FIGS. 4A and 4B show reactivity of B5 and E11 antibodies to HEK293 cells transfected with gene constructs coding for DLA-DR chains by FACS (FIG. 4A) and Western blotting (FIG. 4B).

FIG. 6 shows the amino acid sequences of the heavy and light chains of the murine-canine chimeric cE11 antibody and the nucleotide sequences encoding them.

DETAILED DESCRIPTION

Light (Vk) and heavy (VH) chain variable regions of two antibodies named B5 and E11 are disclosed, which specifically interact with antigens on canine lymphoma and leukemia cells. The B5 antibody contains CDRs of the Vk and VH chains whose amino acid sequences and their corresponding coding nucleotide sequences are disclosed in FIG. 1 as B5Vk and B5VH, while the E11 antibody contains CDRs of the Vk and VH chains whose amino acid sequences and their corresponding coding nucleotide sequences are disclosed in FIG. 2 as E11Vk and E11VH.

B5 and E11 antibodies are produced by hybridoma cells deposited in DSM under access numbers DSM ACC3287 (for B5 antibody) and DSM ACC3288 (for E11 antibody).

Surprisingly, as a result of the selection of monoclonal antibody clones directed against canine B-cell leukemia, clones have been identified which specifically recognize cells of canine B-cell, T-cell and mixed B/T leukemias and lymphomas expressing canine MHC class II antigens (DLA-DR). These antibodies interact with normal T and B lymphocytes, but the expression level of the molecules recognized on these cells is much lower than that of leukemia and lymphoma cells. The antibodies obtained can be used both in diagnosis and treatment of canine leukemias and lymphomas, as well as in other diseases where the expression of the DLA-DR antigen in increased.

One aspect of the invention are two murine monoclonal antibodies B5 and E11, and hybridoma cells secreting these antibodies. Both antibodies have IgG2a heavy chain isotype and recognize conformational epitopes on the DLA-DR molecule.

The DNA and amino acid sequences of the variable regions of each of the antibodies are shown in FIG. 1 and FIG. 2. Example 1 discloses the sequence of variable regions, and Example 4 demonstrates the antibodies' antigen specificity to DLA-DR.

Antibodies obtained by the invention may be labeled with fluorescent dyes, biotin, radionuclides, paramagnetic compounds or enzymes, and used for immunological assays. Example 2 shows staining with biotin-conjugated antibodies, while other types of antibody labeling can easily be obtained by routine prior art methods.

The disclosed antibodies may be used in an ELISA immunoenzyme assay, one of which is used to coat ELISA plates and the other is labeled with biotin or peroxidase as a detection agent. Example 5 describes an example of such an assay.

Figure 7A:
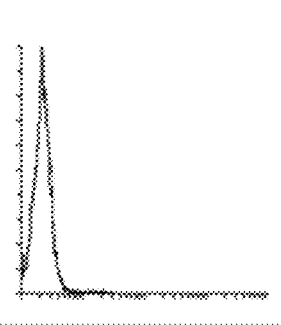
FIG. 7A-7C show reactivity of chimeric murine-canine cE11 antibodies with canine (FIGS. 7A, 7B) and human (FIG. 7C) lymphoma lines.
Figure 7B:
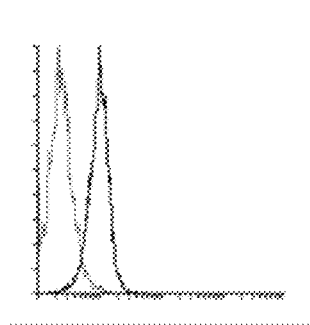
Figure 7C:
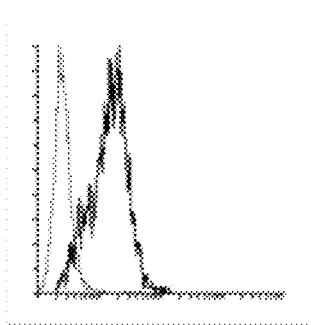

A further aspect of the invention is antibody variable regions, recognizing the antigen, which can be attached to heavy (Fc) and light chain constant regions of canine immunoglobulins to obtain a chimeric murine-canine antibody of reduced immunogenicity for the purpose of canine lymphoma therapy. Example 7 illustrates the method of constructing a murine-canine chimeric antibody based on sequences of variable regions of mouse E11 antibody (disclosed in FIG. 2) and constant regions of canine immunoglobulins. FIG. 7A-7C shows the specificity analysis of the obtained chimeric antibodies using flow cytometry.

A further aspect of the invention is antibody fragments (Fab) obtained by enzymatic proteolysis which may be further conjugated to cytotoxic and/or cytostatic substances (e.g. doxorubicin, betulin, methotrexate) and used in therapy of (canine/human) leukemias and lymphomas or autoimmune diseases.

The B5 and E11 monoclonal antibodies disclosed in this application are the only antibodies that are not based on cross-reactivity between DLA-DR and HLA-DR molecules, but are produced by immunizing mice with canine antigens, which guarantees optimum affinity to the target antigen. Example 2 demonstrates that the fluorescence level obtained after binding the same amount of B5 and E11 antibodies to the DLA-DR antigens present on dog-derived lines is significantly higher than on human lines expressing HLA-DR antigen, indicating optimal affinity to DLA-DR.

IgG2a heavy chain isotype of both antibodies, due to the optimal binding of complement components and Fc receptors on immune cells, allows for antibody-dependent cytotoxic effects. There are also the only available anti-DLA-DR murine antibodies with IgG2a isotype. Example 6 illustrates the cytotoxicity level in an in vitro assay with rabbit complement and indicates that both antibodies exhibit activity in this assay.

The diagnostic potential in canine lymphomas and B-cell and mixed B/T-cell leukemias for the combined use of B5 and E11 antibodies exceeds 94% and is significantly higher than for other available antibodies. Example 3 indicates that the use of B5 and E11 antibodies allows a specific diagnosis of more than 94% of B-cell or mixed B/T neoplasms in lymph nodes using fine needle aspiration biopsy (which is currently the accepted standard of diagnostic procedure). It has been shown, however, that biopsies from enlarged lymph nodes of dogs not suffering from lymphoma or B-type leukemia or of dogs with Lyme disease do not yield a positive reaction with B5 and E11 antibodies.

B5 and E11 MAbs recognize soluble forms of DLA-DR antigens in the ELISA, which is not characteristic of all antibodies reacting with cell membrane-associated HLA-DR molecules. Example 5 confirms the potential of B5 and E11 antibodies to bind DLA-DR antigens present in body fluids or tumor cell lysates.

EXAMPLES

Example 1. Hybridoma generation and DNA sequencing of genes encoding light and heavy chain variable regions of the secreted antibodies, specifically interacting with canine B-cell lymphoma cells.

A standard, commonly described procedure of mice immunization and splenocyte fusion was used to generate monoclonal antibody-producing hybridomas. Briefly, $6 \times 10^6$ cells of canine B-cell lymphoma (CLB70) were suspended in 300 microliters of saline and emulsified in 300 microliters of incomplete Freund's adjuvant. Such prepared antigen was administered in three intraperitoneal injections of 200 microliters/injection to CD-1 mice at two-week intervals. Four days after the last injection, splenocytes of the immunized mice were fused in the presence of polyethylene glycol (PEG 1500) with myeloma SP2.0 line and cultured in the presence of selection medium containing hypoxanthine, aminopterin and thymidine at 37° C. in atmosphere containing 5% $CO_2$. Supernatants from hybridoma culture (500 clones) were screened for reactivity with CLB70 cells using flow cytometry.

In the pool of the analyzed hybridomas, unexpectedly, two lines were identified that produced monoclonal antibodies with very high affinity to canine B-cell lymphomas (CLB70). These antibodies were named B5 and E11, and hybridomas producing them—IITD PAN B5 and IITD PAN E11, respectively. These hybridomas were deposited on Feb. 10, 2016, in accordance with the Budapest Treaty, in the DSMZ (German Collection of Microorganisms and Cell Cultures), having an address of Inhoffenstraße 7B, 38124 Braunschweig, Germany, under the following access numbers: DSM ACC3287 (line IITD PAN B5) and DSM ACC3288 (line IITD PAN E11).

mRNAs were isolated from selected hybridomas producing the antibodies of interest, which, following transcription into cDNA using standard methods of molecular biology, were amplified with oligonucleotide primers of sequences complementary to the regions:

(SEQ ID NO: 21)
$V_k$(5'-CCAGTTCCGAGCTCGTGCTCACCCAGTATACA)
and (SEQ ID NO: 22)
$V_H$(5'-AGGTCCAGCTGCTCGAGTCTGG)
and (SEQ ID NO: 23)
$C_H$ 5'-GCGTCTAGAAYCTCCACACACAGGRRCCAGTGGATAGAC
and (SEQ ID NO: 23)
$C_k$ 5'-GCGTCTAGAACTGGATGGTGGGAAGATGG of murine immunoglobulin. The obtained cDNA fragments were cloned and sequenced using Sanger method. FIG. 1 and FIG. 2 show DNA sequences encoding the heavy chain VH and light chain Vk variable regions of B5 and E11 immunoglobulin. Kabat nomenclature was used in the positioning of amino acids corresponding to variable regions of immunoglobulins. Hypervariable regions in the amino acid sequence are given in bold type and CDR-1, -2, -3 were described accordingly.

Example 2. Reactivity analysis of B5 and E11 antibodies with surface antigens present on selected canine and human cell lines by flow cytofluorimetry.

Figure 3A:
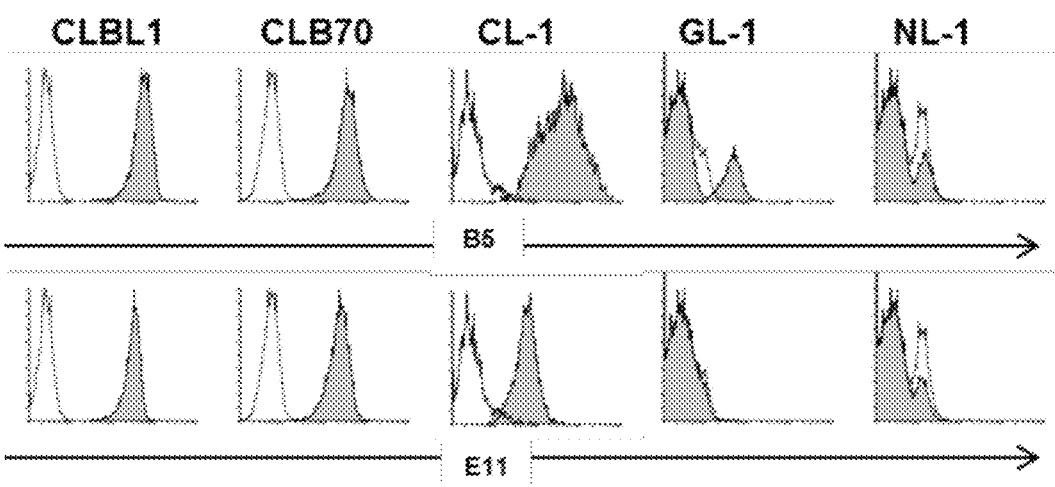
FIGS. 3A and 3B show FACS analysis of canine and human cell lines with B5 and E11 antibodies.
Figure 3B:
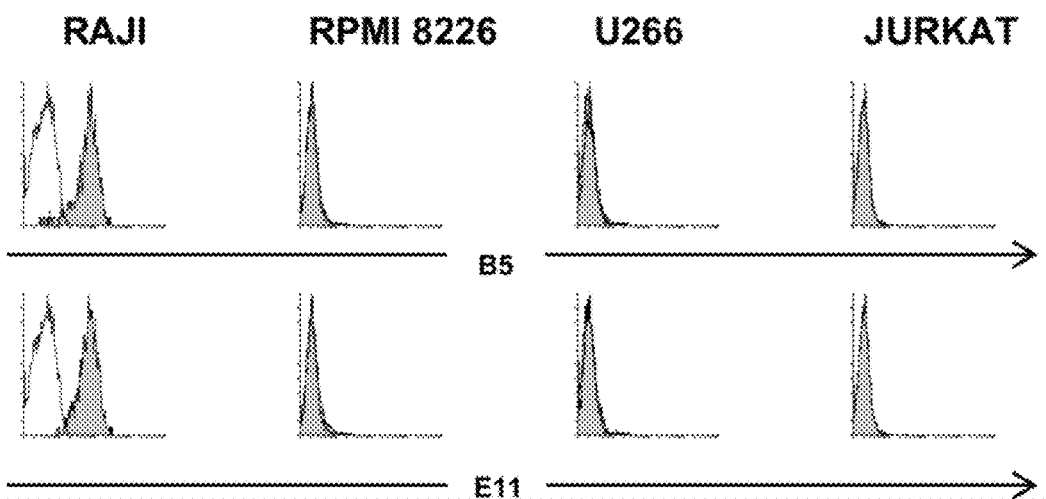

Biotinylated B5 and E11 antibodies or biotinylated mouse anti-DNP control antibody in amount of 1.5 micrograms per 100 microliters of buffered saline (PBS) supplemented with 2% fetal bovine serum (FBS) were incubated with suspensions of $10^5$ cells indicated in FIG. 3A and FIG. 3B on ice for 30 minutes. After washing of unbound antibodies with PBS+2% FBS, the cells were incubated in 100 microliters per sample with a fluorescent conjugate of streptavidin with phycoerythrin (Streptavidin PE, eBioscience) diluted 1:1000. Cytofluorimetry was performed using BD Calibur device. Results are shown as histograms (gray fill) referring to fluorescence of cells stained with control antibody (no fill). These analyzes have shown that antigens recognized by B5 and E11 antibodies are present on the surface of the canine (CLBL1 and CLB70) and human (Raji) lines of B-cell lymphomas, which have, documented in other publications, expression of MHC II haplotype DRB antigens; however, the antigens are absent on canine (GL-1) and human (Jurkat) T-cell lines and canine mastocytoma line (NL-1). Canine GL-1 line with B and T lymphocyte markers, but lacking MHC class II antigens, interacts poorly with B5 antibody and does not interact with E11 at all.

Example 3. Reactivity analysis of B5 and E11 antibodies with blood samples and dog lymph node biopsies.

The obtained suspensions of mononuclear cells from peripheral blood (PBMCs) (Table 1) or from lymph node biopsies (Table 2) of dogs with diagnosed lymphomas or enlarged as a result of confirmed *Borrelia burgdorferi* infection were stained as in Example 2 and subjected to FACS cytofluorimetry. Percentage of PBMCs with B5 and E11 mAb reactivity was the highest for B-cell lymphoma cases and was three out of three analyzed for B5 mAb and two out of three for E1 mAb, respectively (Table 1). However, no reactivity of either antibody was reported for samples from healthy dogs, dogs infected with *Borrelia burgdorferi* or diagnosed with T-cell lymphomas. Percentage of lymph node cells with specific fluorescence, above the isotype control fluorescence (>15% positive cells), are summarized in Table 2, separately for each dog. For 13 patients with confirmed B-cell lymphomas, 11 (84.6%) and 12 (92.3%) showed reactivity with B5 and E11 antibodies, respectively. Among dogs with T-cell lymphomas these values were respectively 1 in 5 with B5 mAb (20%) and 0 in 5 with E11 mAb. For 5 analyzed lymphomas of mixed B/T-cell phenotype, 5 (100%) were positive for B5 mAb and 4 (80%) for E11 mAb. Table 3 evaluates the expression level of antigens recognized by B5 and E11 mAbs. It was demonstrated that the highest mean fluorescence intensity (MFI) of 539 and 294 was shown by mixed B/T-cell and B-cell lymphomas stained with B5 antibody, respectively. For E11 antibody, these values were respectively 308 and 162. The MFI for T-cell lymphomas was 23 and 15 for B5 and E11 antibodies, respectively. The MFI values for PBMCs from healthy dogs or patients with Lyme disease did not exceed 10.5.

Example 4. Identification of antigens recognized by B5 and E11 antibodies.

Based on the sequencing of immunoprecipitated proteins from CLBL1 line lysates by mass spectrometry, histocompatibility class II antigen dimers, DLA-DRs, were provisionally pre-selected as specifically bound by B5 and E11 antibodies. In order to confirm this identification, human fetal carcinoma line (HEK293) was transfected with gene constructs encoding canine DLA-DRα and DLA-DRβ histocompatibility antigen chains in pcDNA3 expression vector or control empty expression vector. Briefly, 3 μg of purified plasmid DNA were incubated with Metafecten® Pro reagent (Biontex) according to the manufacturer's protocol and then DNA/Metafecten® Pro mixture was introduced into $2 \times 10^5$ HEK293 cells cultured on a 12-well plate in 1 ml of OptiMEM™ medium (Life Technologies). 24 hours after transfection, the cells were analyzed with FACS cytofluorimetry using B5 and E11 antibodies as described in Example 2. FIG. 4A shows an exemplary, representative FACS analysis of cells after transfection. Cells transfected with single control constructs (pcDNA3) or encoding either DLA-DRα or DLA-DRβ chains did not stain with fluorescent conjugates of B5 and E11 antibodies, while staining was demonstrated for both antibodies in case of co-transfection of HEK293 cells with constructs coding for DLA-DRα and DLA-DRβ chains.

Using Western blotting technique on protein lysates from cells transfected with the gene constructs described above, that B5 and E11 antibodies have been shown to recognize the DLA-DRαβ dimer with a molecular weight of 55 kD, but do not recognize single DLA-DRα or DLA-DRβ chains (FIG. 4B). Furthermore, reactivity of both antibodies in Western blotting with lysates from B-cell lymphoma lines (CLBL1 and CLB70) was demonstrated, but not with lysates from B-cell line (GL-1) lacking DLA-DR antigens, as well as with lysates from peripheral blood mononuclear cells PBMCs (FIG. 4B). Moreover, it has been established that the epitopes recognized by B5 and E11 antibodies are conformational, as the treatment of protein lysates with 6 M urea solution or boiling them at temperatures above 70° C. abolished the antibody-antigen interaction.

Example 5. DLA-DR and S-DLA-DR ELISA on cell lysates and body fluids based on the use of B5 and E11 antibodies.

Figure 5:
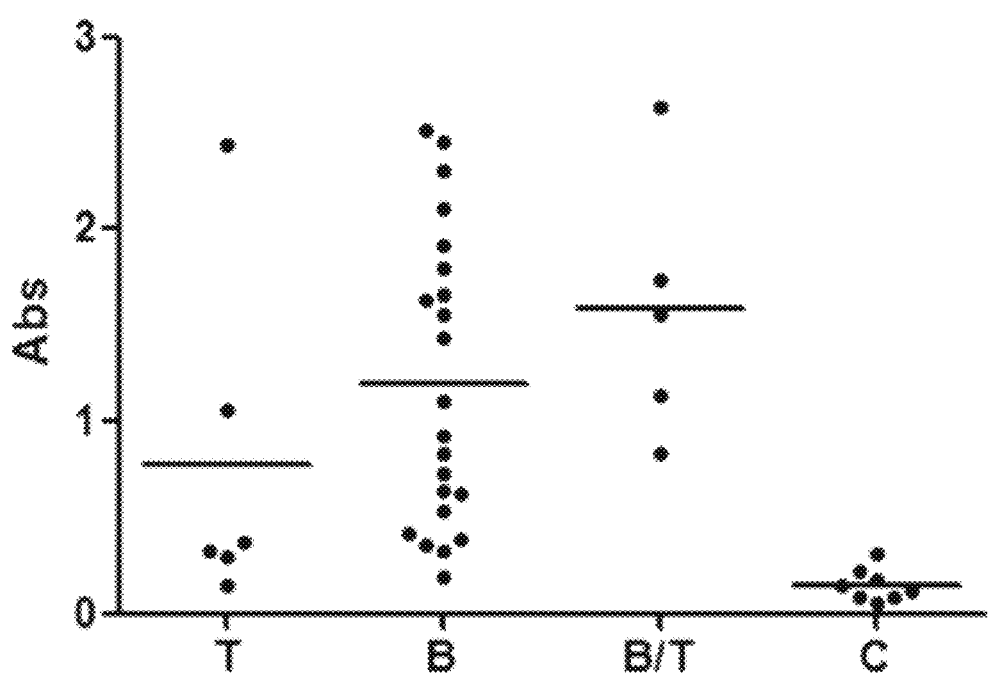
FIG. 5 shows detection of DLA-DR molecules in lysates from lymph node biopsies of healthy dogs (C) and dogs with B-cell (B), T-cell (T) and B/T (B/T) lymphomas.

ELISA plates (Maxisorp™, Nunc) were coated with a solution of E11 antibody at 2 μg/ml PBS at 4° C. for 12 hours. After blocking the plate with 1% solution of casein in TBS buffer (50 mM tris(hydroxymethyl)aminomethane (Tris)-Cl, pH 7.5, 150 mM NaCl) with 0.05% Tween®-20 detergent for 1 hour at 37° C., plates were incubated with test solutions (cell lysate, blood serum) for 1 hour at 37° C., then washed 3 times with TBS+0.05% Tween®-20 and incubated with biotinylated B5 antibody (1.5 μg/ml) for 1 hour at 37° C. After washing three times, as described above, plates were incubated with streptavidin-horseradish peroxidase conjugate (1:1000, eBioscience) for 1 hour at 37° C., followed by a colored reaction by adding TMB substrate. Table 4 shows that lysates from cells expressing DLA-DR histocompatibility antigens demonstrate approximately 40 times higher specific ELISA absorbance versus control cells, and that blood sera from dogs with lymphoma show on average twice higher specific absorbance in this assay in relation to the controls. FIG. 5 shows results of the ELISA test with lysates from lymph node biopsies from healthy dogs and patients with B-cell, T-cell and B/T lymphomas. More than 85% of the lysates from diseased dogs give a positive result.

Example 6. Complement-dependent cytotoxicity analysis for B5 and E11 antibodies against canine lymphoma CLBL1.

Canine CLBL-1 lymphoma cells (2×10) were incubated with B5 or E11 antibodies at a concentration of 1 μg/100 μl for 1 hour on ice in RPMI medium without serum. After centrifugation of the cells (300×g for 5 minutes) and antibody washing (5 ml of RPMI medium), the cells were suspended in 1 ml of RPMI medium supplemented with 50 μl of non-toxic rabbit complement (Sigma). Cells with complement were incubated for 40 minutes in 37° C. water bath with periodic mixing of the sample every 10 minutes. After incubation, the cells were centrifuged (300×g for 5 minutes), washed with PBS+2% FBS and the viability was assayed by incubation with propidium iodide (50 ng/ml) in a FACS cytofluorimetic assay. Dead and live cells were also counted in Burker's chamber using trypan blue staining. Table 5 shows that B5 and E11 antibodies, but not a murine control antibody of the same isotype as B5 and E11, exhibit a complement-dependent cytotoxic effect.

Example 7. Construction method and specificity analysis of murine-canine chimeric antibody (cE11) based on sequences using variable regions of murine E11 antibody.

mRNA molecules encoding heavy and light chain variable regions were isolated from the E11 hybridoma using Trizol™ reagent (Thermofisher Scientific). Rapid reaction of mRNA transcription into cDNA was performed using MMLV reverse transcriptase enzyme using oligonucleotide primers complementary to 3' portions of heavy chain $V_H$ 5'-GCGTCTAGAAYCTCCACACACAGGRRCCAGTG-GATAGAC or light chain $V_L$ 5'-GCGTCTAGAACTG-GATGGTGGGAAGATGG variable regions of murine immunoglobulins. The resulting PCR products were cloned by TA method into pGEM T-easy vector (Promega) and sequenced.

Fragments of mRNA molecules encoding constant regions of canine immunoglobulins were obtained by mRNA isolation from dog peripheral blood leukocytes with Trizol™ reagent (Thermofisher Scientific), transcription into cDNA and amplification by PCR using the following oligonucleotide primers:

Heavy chain constant region of canine Ig (cIgH)
HCANISF
5'-CTCAGCCTCCACCACG

HCANISR
5'-CAGGATCCTCATTTACCCGGAGAATGG

Light chain constant region of canine Ig (cIgL)
LCANISF
5'-CTTGTTCCAACCATCTCCAG

LCANISR
5'-CACTTGCTAGCTTAGTCCACTCTCTGACACTCG.

Using the PCR described below, murine and canine cDNA regions encoding immunoglobulin variable and constant chains were amplified. Murine and canine amplicons contained complementary regions which allowed to produce chimeric molecules in subsequent amplification cycles using the following oligonucleotide primers:

Heavy chain variable region of murine Ig (mIgH)
(SEQ ID NO: 31)
HE11F CTTCCGGAATGGGATGGAGCTGGATC (SEQ ID NO: 32)
HE1R *CGTGGTGGAGGCTGAGGAGACGGTGACTGAGGTTC*
(the fragment complementary to HCANISF primer is given in italic font)

Light chain variable region of murine Ig (mIgL)
(SEQ ID NO: 33)
LE11F GCCAGATCTATGAGTGTGCCCACTC (SEQ ID NO: 34)
LE11R *CTGGAGATGGTTGGAACAAGGATACAGTTGGTGCAGC*
(the fragment complementary to LCANISF primer is given in italic font).

The PCR reaction using high-fidelity KapaTaq HiFi polymerase (Kapa Biosystems) was performed under the following temperature conditions:
98° C. 3 min
95° C. 20 sec.
52° C. 15 sec.
72° C. 20 sec.
72° C. 1 minute
10° C. ∞

Amplified DNA fragments were cloned into pVitro neo vector (Invivogen) using BspEI and BamHI restriction sites for the heavy chain and BglII and NheI for the light chain and taking advantage of the presence of suitable restriction sites in amplified cDNA fragments for murine-canine immunoglobulins.

The amino acid sequences of both chains of the resulting chimeric cE11 antibody (i.e., the caninized E11 antibody) and the nucleotide sequences encoding them are shown in FIG. 6. Moreover, the sequence listing shows the heavy chain constant region of canine immunoglobulin and the light chain constant region of canine immunoglobulin, which were used to obtain the chimeric cE11 antibody.

The generated constructs were transfected into cells of CHO line by lipofection with Lipofectamine 2000 (Life Technologies). After 48 hours, supernatants from the cultures were screened for antibodies interacting with canine lymphoma lines (FIG. 7A and FIG. 7B).

The invention claimed is:

1. An antibody that specifically binds to DLA-DR antigen on canine lymphoma and leukemia cells, the antibody comprising:
   A) an antibody heavy chain comprising CDR regions designated as SEQ ID Nos. 1-3, and
   an antibody light chain comprising CDR regions designated as SEQ ID Nos. 9-11,
   or
   B) an antibody heavy chain comprising CDR regions designated as SEQ ID Nos. 4-6, and
   an antibody light chain comprising CDR regions designated as SEQ ID Nos. 12-14.

2. The antibody of claim 1, wherein the antibody is a chimeric murine-canine antibody comprising: an antibody heavy chain comprising a heavy chain constant region derived from a canine immunoglobulin, and an antibody light chain comprising a light chain constant region derived from a canine immunoglobulin.

3. The antibody of claim 1, wherein the antibody of A) and B) is produced by a hybridoma cell line deposited in DSMZ under access number DSM ACC3287 and DSM ACC3288, respectively.

4. Hybridoma cell line deposited in DSMZ under access number DSM ACC3287 or DSM ACC3288.

5. A method for treating leukemia or lymphoma, the method comprising administering to a canine subject in need thereof, the antibody of claim 1.

6. A method for diagnosing leukemia or lymphoma in a canine subject, the method comprising detecting whether DLA-DR antigens are present in a sample from the subject by contacting the sample with the antibody of claim 1, and diagnosing the subject with leukemia or lymphoma when the presence of DLA-DR is detected.

* * * * *

SEQUENCE LISTING

<160> NUMBER OF SEQ ID NOS: 40

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B5VH CDR1

<400> SEQUENCE: 1

Ser Tyr Phe Ile His
1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B5VH CDR2

<400> SEQUENCE: 2

Trp Ile Phe Pro Gly Asn Ile Asn Ala Lys Tyr Asn Glu Asn Phe Arg
1               5                   10                  15

Gly

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B5VH CDR3

<400> SEQUENCE: 3

Ala Pro Leu Leu Gly Asn Tyr Phe Asp Tyr
1               5                   10

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: E11VH CDR1

<400> SEQUENCE: 4

Ser Tyr Tyr Ile His
1               5

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: E11VH CDR2

<400> SEQUENCE: 5

Trp Ile Tyr Pro Gly Ser Gly Asn Ser Lys Tyr Asn Glu Lys Phe Lys
1               5                   10                  15

Gly

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: E11VH CDR3

<400> SEQUENCE: 6

Gly Gly Ser Gly Tyr Val Gly Ala Met Asn Cys
1               5                   10

<210> SEQ ID NO 7
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B5VH

<400> SEQUENCE: 7

```
Gln Val Gln Leu Gln Gln Ser Gly Pro Glu Leu Met Lys Pro Gly Thr
1               5                   10                  15

Ser Val Lys Ile Ser Cys Lys Ala Ser Gly Tyr Thr Phe Thr Ser Tyr
                20                  25                  30

Phe Ile His Trp Met Lys Gln Arg Pro Gly Gln Gly Leu Glu Trp Ile
            35                  40                  45

Gly Trp Ile Phe Pro Gly Asn Ile Asn Ala Lys Tyr Asn Glu Asn Phe
    50                  55                  60

Arg Gly Lys Ala Thr Leu Thr Ala Asp Thr Ser Thr Thr Ala Tyr
65                  70                  75                  80

Ile Gln Leu Ser Ser Leu Thr Ser Glu Asp Ser Ala Val Tyr Tyr Cys
                85                  90                  95

Ala Arg Ala Pro Leu Leu Gly Asn Tyr Phe Asp Tyr Trp Gly Gln Gly
                100                 105                 110

Thr Thr Leu Thr Val Ser Ser
            115
```

```
<210> SEQ ID NO 8
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: E11VH

<400> SEQUENCE: 8
```

```
Gln Val Gln Leu Gln Gln Ser Gly Pro Glu Leu Val Lys Pro Gly Thr
1               5                   10                  15

Ser Val Lys Ile Ser Cys Lys Ala Ser Gly Tyr Arg Phe Thr Ser Tyr
                20                  25                  30

Tyr Ile His Trp Val Lys Gln Arg Pro Gly Gln Gly Leu Glu Trp Ile
            35                  40                  45

Gly Trp Ile Tyr Pro Gly Ser Gly Asn Ser Lys Tyr Asn Glu Lys Phe
    50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Val Phe Tyr Cys
                85                  90                  95

Ala Arg Gly Gly Ser Gly Tyr Val Gly Ala Met Asn Cys Trp Gly Gln
                100                 105                 110

Gly Thr Ser Val Thr Val Ser Ser
            115                 120
```

```
<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B5Vk CDR1

<400> SEQUENCE: 9
```

```
Gly Ala Ser Glu Asn Ile Tyr Gly Ala Leu Ser
1               5                   10
```

```
<210> SEQ ID NO 10
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B5Vk CDR2

<400> SEQUENCE: 10

Gly Ala Thr Asn Leu Ala Asp
1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: B5Vk CDR3

<400> SEQUENCE: 11

Gln Asn Phe Phe Ile Thr Pro Tyr Thr
1               5

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: E11Vk CDR1

<400> SEQUENCE: 12

Arg Thr Ser Glu Asn Ile Tyr Ser Phe Leu Ala
1               5                   10

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: E11Vk CDR2

<400> SEQUENCE: 13

Asn Ala Lys Thr Leu Val Glu
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: E11Vk CDR3

<400> SEQUENCE: 14

Gln His His Tyr Gly Thr Pro Leu Thr
1               5
```

```
<210> SEQ ID NO 15
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: B5Vk

<400> SEQUENCE: 15

Glu Leu Val Leu Thr Gln Ser Pro Ala Ser Leu Ser Ala Ser Val Gly
1               5                   10                  15

Glu Thr Val Thr Ile Thr Cys Gly Ala Ser Glu Asn Ile Tyr Gly Ala
            20                  25                  30

Leu Ser Trp Tyr Gln Arg Lys Gln Gly Lys Ser Pro Gln Leu Leu Ile
        35                  40                  45

Tyr Gly Ala Thr Asn Leu Ala Asp Gly Leu Ser Ser Arg Phe Ser Gly
    50                  55                  60

Ser Gly Ser Gly Arg Gln Tyr Ser Leu Lys Ile Ser Ser Leu His Pro
65                  70                  75                  80

Asp Asp Val Ala Thr Tyr Tyr Cys Gln Asn Phe Phe Ile Thr Pro Tyr
                85                  90                  95

Thr Phe Gly Gly Gly Thr Lys Leu Glu Met Lys Arg
            100                 105

<210> SEQ ID NO 16
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: E11Vk

<400> SEQUENCE: 16

Asp Ile Gln Met Thr Gln Ser Pro Ala Ser Leu Ser Ala Ser Val Gly
1               5                   10                  15

Glu Thr Val Thr Ile Thr Cys Arg Thr Ser Glu Asn Ile Tyr Ser Phe
            20                  25                  30

Leu Ala Trp Ser Gln Gln Lys Gln Gly Lys Ser Pro Gln Leu Leu Val
        35                  40                  45

Tyr Asn Ala Lys Thr Leu Val Glu Gly Val Pro Ser Arg Phe Ser Gly
    50                  55                  60

Ser Gly Ser Gly Thr Gln Phe Ser Leu Arg Ile Asn Ser Leu Gln Pro
65                  70                  75                  80

Glu Asp Phe Gly Ser Tyr Tyr Cys Gln His His Tyr Gly Thr Pro Leu
                85                  90                  95

Thr Phe Gly Ala Gly Thr Lys Leu Glu Val Lys Arg
            100                 105

<210> SEQ ID NO 17
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: B5VH cDNA

<400> SEQUENCE: 17
```

```
caggtccaac tgcaacagtc tggacctgaa ctgatgaagc ctgggacttc agtgaagatt      60
tcctgcaagg cttctggcta cactttcaca agctacttta tacactggat gaagcagagg     120
cctggacagg gacttgagtg gattggatgg attttcctg gaaatattaa tgctaaatat      180
aatgagaact tcagggggcaa ggccacactg acggcagaca catcctccac caccgcctac    240
atacagctca gcagcctaac atctgaggac tctgcggtct attactgtgc aagagcccct    300
ttactgggga actactttga ctactggggc caaggcacca ctctcacagt ctcctca       357
```

<210> SEQ ID NO 18
<211> LENGTH: 324
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: B5Vk cDNA

<400> SEQUENCE: 18

```
gagctcgtgc tcacccagtc tccagcttca ctgtctgcat ctgtgggaga aactgtcacc      60
atcacatgtg agcaagtga gaatatttac ggtgctttaa gttggtatca gcggaaacag     120
ggcaagtctc ctcagctcct gatctatggt gcaaccaact ggcagatggg cttgtcatcg    180
aggttcagtg gcagtggatc tggtagacag tattctctca agatcagtag cctgcatcct    240
gacgatgttg caacgtatta ctgtcaaaat ttttttatta ctccgtacac gttcggaggg    300
gggaccaagc tggaaatgaa acgg                                            324
```

<210> SEQ ID NO 19
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: E11VH cDNA

<400> SEQUENCE: 19

```
caggtccagc tgcagcagtc tggacctgaa ctggtgaagc ctgggacttc agtgaagata      60
tcctgcaagg cttctggcta caggttcaca agctactata tacactgggt gaagcagagg     120
cctggacagg gacttgagtg gattggatgg atttatcctg gaagtggcaa tagtaagtac    180
aatgagaagt tcaagggcaa ggccacactg acggcagaca catcctccag cactgcctac    240
atgcagctca gcagcctaac atctgaggac tctgcggtct tttactgtgc aagaggtggc    300
tcaggctacg taggggctat gaactgctgg ggtcaaggaa cctcagtcac cgtctcctca    360
```

<210> SEQ ID NO 20
<211> LENGTH: 324
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: E11Vk cDNA

<400> SEQUENCE: 20

```
gacatccaga tgactcagtc tccagcctcc ctatctgcat ctgtgggaga aactgtcacc      60
atcacatgtc gaacaagtga gaatatttac agttttttag catggtctca gcagaaacag     120
```

```
ggaaaatctc ctcagctcct ggtctataat gcaaaaacct tagtagaagg tgtgccatca    180
aggttcagtg gcagtggatc aggcacacag ttttctctga ggatcaacag cctgcagcct    240
gaagattttg gagttatta ctgtcaacat cattatggta ctcctctcac gttcggcgct    300
gggaccaagc tggaggtgaa acgg                                           324
```

<210> SEQ ID NO 21
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Vk

<400> SEQUENCE: 21

```
ccagttccga gctcgtgctc acccagtata ca                                   32
```

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: primer VH

<400> SEQUENCE: 22

```
aggtccagct gctcgagtct gg                                              22
```

<210> SEQ ID NO 23
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: primer CH

<400> SEQUENCE: 23

```
gcgtctagaa yctccacaca caggrrccag tggatagac                            39
```

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: primer Ck

<400> SEQUENCE: 24

```
gcgtctagaa ctggatggtg ggaagatgg                                       29
```

<210> SEQ ID NO 25
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: primer VH from example 7

```
<400> SEQUENCE: 25
gcgtctagaa yctccacaca caggrrccag tggatagac                              39

<210> SEQ ID NO 26
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: primer VL from example 7

<400> SEQUENCE: 26
gcgtctagaa ctggatggtg ggaagatgg                                          29

<210> SEQ ID NO 27
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: primer HCANISF

<400> SEQUENCE: 27
ctcagcctcc accacg                                                        16

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: primer HCANISR

<400> SEQUENCE: 28
caggatcctc atttacccgg agaatgg                                            27

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: primer LCANISF

<400> SEQUENCE: 29
cttgttccaa ccatctccag                                                    20

<210> SEQ ID NO 30
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: primer LCANISR

<400> SEQUENCE: 30
cacttgctag cttagtccac tctctgacac tcg                                     33
```

<210> SEQ ID NO 31
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: primer HE11F

<400> SEQUENCE: 31
cttccggaat gggatggagc tggatc                                          26

<210> SEQ ID NO 32
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: primer HE11R

<400> SEQUENCE: 32
cgtggtggag gctgaggaga cggtgactga ggttc                                35

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: primer LE11F

<400> SEQUENCE: 33
gccagatcta tgagtgtgcc cactc                                           25

<210> SEQ ID NO 34
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: primer LE11R

<400> SEQUENCE: 34
ctggagatgg ttggaacaag gatacagttg gtgcagc                              37

<210> SEQ ID NO 35
<211> LENGTH: 1425
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cE11 heavy chain cDNA

<400> SEQUENCE: 35
atgggatgga gctggatctt tctcttcctc ctgtcaggaa ctgcaggtgt ccattgccag      60
gtccagctgc agcagtctgg acctgaactg gtgaagcctg ggacttcagt gaagatatcc    120
tgcaaggctt ctggctacag gttcacaagc tactatatac actgggtgaa gcagaggcct    180

```
ggacagggac ttgagtggat tggatggatt tatcctggaa gtggcaatag taagtacaat    240
gagaagttca agggcaaggc cacactgacg gcagacacat cctccagcac tgcctacatg    300
cagctcagca gcctaacatc tgaggactct gcggtctttt actgtgcaag aggtggctca    360
ggctacgtag ggctatgaa ctgctggggt caaggaacct cagtcaccgt ctcctcagcc     420
```
```
tccaccacgg cccctcggt tttcccactg gccccagct gcgggtccac ttccggctcc      480
acggtggccc tggcctgcct ggtgtcaggc tacttcccg agcctgtaac tgtgtcctgg     540
aattccggct ccttgaccag cggtgtgcac accttcccgt ccgtcctgca gtcctcaggg   600
ctctactccc tcagcagcat ggtgacagtg ccctccagca ggtggcccag cgagaccttc   660
acctgcaacg tggcccaccc ggccagcaaa actaaagtag acaagccagt gcccaaaaga   720
gaaaatggaa gagttcctcg cccacctgat tgtcccaaat gcccagcccc tgaaatgctg   780
ggagggcctt cggtcttcat ctttcccccg aaacccaagg acaccctctt gattgcccga   840
acacctgagg tcacatgtgt ggtggtggat ctggacccag aagaccctga ggtgcagatc   900
agctggttcg tggacggtaa cagatgcaa acagccaaga ctcagcctcg tgaggagcag    960
ttcaatggca cctaccgtgt ggtcagtgtc ctccccattg gcaccagga ctggctcaag    1020 gggaagcagt tcacgtgcaa agtcaacaac aaagccctcc catccccgat cgagaggacc   1080
atctccaagg ccagagggca agcccatcag cccagtgtgt atgtcctgcc gccatcccgg   1140
gaggagttga gcaagaacac agtcagcttg acatgcctga tcaaagactt cttcccacct   1200
gacattgatg tggagtggca gagcaatgga cagcaggagc tgagagcaa gtaccgcacg    1260 accccgcccc agctggacga ggacgggtcc tacttcctgt acagcaagct ctctgtggac   1320
aagagccgct ggcagcgggg agacaccttc atatgtgcgg tgatgcatga agctctacac   1380
aaccactaca cacaggaatc cctctcccat tctccgggta aatga                   1425

<210> SEQ ID NO 36
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cE11 light chain cDNA

<400> SEQUENCE: 36
atgagtgtgc ccactcaggt cctggggttg ctgctgctgt ggcttacagg tgccagatgt     60
gacatccaga tgactcagtc tccagcctcc ctatctgcat ctgtgggaga aactgtcacc   120
atcacatgtc gaacaagtga gaatatttac agtttttag catggtctca gcagaaacag   180
ggaaaatctc ctcagctcct ggtctataat gcaaaaacct tagtagaagg tgtgccatca   240
aggttcagtg gcagtggatc aggcacacag ttttctctga ggatcaacag cctgcagcct   300
gaagattttg ggagttatta ctgtcaacat cattatggta ctcctctcac gttcggcgct   360
gggaccaagc tggaggtgaa acgggctgat gctgcaccaa ctgtatcctt gttccaacca   420
tctccagacc agttacacac aggaagtgcc tctgttgtgt gtttgctgaa tagcttctac   480
cccaaagaca tcaatgtcaa gtggaaagtg gatggtgtca tccaagacac aggcatccag   540
gaaagtgtca cagagcagga caaggacagt acctacagcc tcagcagcac cctgacgatg   600
tccagtactg agtacctaag tcatgagttg tactcctgtg agatcactca caagagcctg   660
ccctccaccc tcatcaagag cttccaaagg agcgagtgtc agagagtgga ctaa           714
```

<210> SEQ ID NO 37
<211> LENGTH: 474
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cE11 heavy chain

<400> SEQUENCE: 37

```
Met Gly Trp Ser Trp Ile Phe Leu Phe Leu Leu Ser Gly Thr Ala Gly
 1               5                  10                  15

Val His Cys Gln Val Gln Leu Gln Gln Ser Gly Pro Glu Leu Val Lys
            20                  25                  30

Pro Gly Thr Ser Val Lys Ile Ser Cys Lys Ala Ser Gly Tyr Arg Phe
        35                  40                  45

Thr Ser Tyr Tyr Ile His Trp Val Lys Gln Arg Pro Gly Gln Gly Leu
    50                  55                  60

Glu Trp Ile Gly Trp Ile Tyr Pro Gly Ser Gly Asn Ser Lys Tyr Asn
65                  70                  75                  80

Glu Lys Phe Lys Gly Lys Ala Thr Leu Thr Ala Asp Thr Ser Ser Ser
                85                  90                  95

Thr Ala Tyr Met Gln Leu Ser Ser Leu Thr Ser Glu Asp Ser Ala Val
            100                 105                 110

Phe Tyr Cys Ala Arg Gly Gly Ser Gly Tyr Val Gly Ala Met Asn Cys
        115                 120                 125

Trp Gly Gln Gly Thr Ser Val Thr Val Ser Ser Ala Ser Thr Thr Ala
    130                 135                 140

Pro Ser Val Phe Pro Leu Ala Pro Ser Cys Gly Ser Thr Ser Gly Ser
145                 150                 155                 160

Thr Val Ala Leu Ala Cys Leu Val Ser Gly Tyr Phe Pro Glu Pro Val
                165                 170                 175

Thr Val Ser Trp Asn Ser Gly Ser Leu Thr Ser Gly Val His Thr Phe
            180                 185                 190

Pro Ser Val Leu Gln Ser Ser Gly Leu Tyr Ser Leu Ser Ser Met Val
        195                 200                 205

Thr Val Pro Ser Ser Arg Trp Pro Ser Glu Thr Phe Thr Cys Asn Val
    210                 215                 220

Ala His Pro Ala Ser Lys Thr Lys Val Asp Lys Pro Val Pro Lys Arg
225                 230                 235                 240

Glu Asn Gly Arg Val Pro Arg Pro Pro Asp Cys Pro Lys Cys Pro Ala
                245                 250                 255

Pro Glu Met Leu Gly Gly Pro Ser Val Phe Ile Phe Pro Pro Lys Pro
            260                 265                 270

Lys Asp Thr Leu Leu Ile Ala Arg Thr Pro Glu Val Thr Cys Val Val
        275                 280                 285

Val Asp Leu Asp Pro Glu Asp Pro Glu Val Gln Ile Ser Trp Phe Val
    290                 295                 300

Asp Gly Lys Gln Met Gln Thr Ala Lys Thr Gln Pro Arg Glu Glu Gln
305                 310                 315                 320

Phe Asn Gly Thr Tyr Arg Val Val Ser Val Leu Pro Ile Gly His Gln
                325                 330                 335

Asp Trp Leu Lys Gly Lys Gln Phe Thr Cys Lys Val Asn Asn Lys Ala
            340                 345                 350
```

```
Leu Pro Ser Pro Ile Glu Arg Thr Ile Ser Lys Ala Arg Gly Gln Ala
            355                 360                 365

His Gln Pro Ser Val Tyr Val Leu Pro Pro Ser Arg Glu Glu Leu Ser
        370                 375                 380

Lys Asn Thr Val Ser Leu Thr Cys Leu Ile Lys Asp Phe Phe Pro Pro
385                 390                 395                 400

Asp Ile Asp Val Glu Trp Gln Ser Asn Gly Gln Gln Glu Pro Glu Ser
                405                 410                 415

Lys Tyr Arg Thr Thr Pro Pro Gln Leu Asp Glu Asp Gly Ser Tyr Phe
            420                 425                 430

Leu Tyr Ser Lys Leu Ser Val Asp Lys Ser Arg Trp Gln Arg Gly Asp
        435                 440                 445

Thr Phe Ile Cys Ala Val Met His Glu Ala Leu His Asn His Tyr Thr
    450                 455                 460

Gln Glu Ser Leu Ser His Ser Pro Gly Lys
465                 470

<210> SEQ ID NO 38
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cE11 light chain

<400> SEQUENCE: 38

Met Ser Val Pro Thr Gln Val Leu Gly Leu Leu Leu Leu Trp Leu Thr
1               5                   10                  15

Gly Ala Arg Cys Asp Ile Gln Met Thr Gln Ser Pro Ala Ser Leu Ser
            20                  25                  30

Ala Ser Val Gly Glu Thr Val Thr Ile Thr Cys Arg Thr Ser Glu Asn
        35                  40                  45

Ile Tyr Ser Phe Leu Ala Trp Ser Gln Gln Lys Gln Gly Lys Ser Pro
    50                  55                  60

Gln Leu Leu Val Tyr Asn Ala Lys Thr Leu Val Glu Gly Val Pro Ser
65                  70                  75                  80

Arg Phe Ser Gly Ser Gly Ser Gly Thr Gln Phe Ser Leu Arg Ile Asn
                85                  90                  95

Ser Leu Gln Pro Glu Asp Phe Gly Ser Tyr Tyr Cys Gln His His Tyr
            100                 105                 110

Gly Thr Pro Leu Thr Phe Gly Ala Gly Thr Lys Leu Glu Val Lys Arg
        115                 120                 125

Ala Asp Ala Ala Pro Thr Val Ser Leu Phe Gln Pro Ser Pro Asp Gln
    130                 135                 140

Leu His Thr Gly Ser Ala Ser Val Val Cys Leu Leu Asn Ser Phe Tyr
145                 150                 155                 160

Pro Lys Asp Ile Asn Val Lys Trp Lys Val Asp Gly Val Ile Gln Asp
                165                 170                 175

Thr Gly Ile Gln Glu Ser Val Thr Glu Gln Asp Lys Asp Ser Thr Tyr
            180                 185                 190

Ser Leu Ser Ser Thr Leu Thr Met Ser Ser Thr Glu Tyr Leu Ser His
        195                 200                 205

Glu Leu Tyr Ser Cys Glu Ile Thr His Lys Ser Leu Pro Ser Thr Leu
    210                 215                 220
```

Ile Lys Ser Phe Gln Arg Ser Glu Cys Gln Arg Val Asp
225                 230                 235

<210> SEQ ID NO 39
<211> LENGTH: 336
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cE11 constant (canine) part of heavy chain

<400> SEQUENCE: 39

Ser Ala Ser Thr Thr Ala Pro Ser Val Phe Pro Leu Ala Pro Ser Cys
1               5                   10                  15

Gly Ser Thr Ser Gly Ser Thr Val Ala Leu Ala Cys Leu Val Ser Gly
            20                  25                  30

Tyr Phe Pro Glu Pro Val Thr Val Ser Trp Asn Ser Gly Ser Leu Thr
        35                  40                  45

Ser Gly Val His Thr Phe Pro Ser Val Leu Gln Ser Ser Gly Leu Tyr
    50                  55                  60

Ser Leu Ser Ser Met Val Thr Val Pro Ser Ser Arg Trp Pro Ser Glu
65                  70                  75                  80

Thr Phe Thr Cys Asn Val Ala His Pro Ala Ser Lys Thr Lys Val Asp
                85                  90                  95

Lys Pro Val Pro Lys Arg Glu Asn Gly Arg Val Pro Arg Pro Pro Asp
            100                 105                 110

Cys Pro Lys Cys Pro Ala Pro Glu Met Leu Gly Gly Pro Ser Val Phe
        115                 120                 125

Ile Phe Pro Pro Lys Pro Lys Asp Thr Leu Leu Ile Ala Arg Thr Pro
    130                 135                 140

Glu Val Thr Cys Val Val Val Asp Leu Asp Pro Glu Asp Pro Glu Val
145                 150                 155                 160

Gln Ile Ser Trp Phe Val Asp Gly Lys Gln Met Gln Thr Ala Lys Thr
                165                 170                 175

Gln Pro Arg Glu Glu Gln Phe Asn Gly Thr Tyr Arg Val Val Ser Val
            180                 185                 190

Leu Pro Ile Gly His Gln Asp Trp Leu Lys Gly Lys Gln Phe Thr Cys
        195                 200                 205

Lys Val Asn Asn Lys Ala Leu Pro Ser Pro Ile Glu Arg Thr Ile Ser
    210                 215                 220

Lys Ala Arg Gly Gln Ala His Gln Pro Ser Val Tyr Val Leu Pro Pro
225                 230                 235                 240

Ser Arg Glu Glu Leu Ser Lys Asn Thr Val Ser Leu Thr Cys Leu Ile
                245                 250                 255

Lys Asp Phe Phe Pro Pro Asp Ile Asp Val Glu Trp Gln Ser Asn Gly
            260                 265                 270

Gln Gln Glu Pro Glu Ser Lys Tyr Arg Thr Thr Pro Pro Gln Leu Asp
        275                 280                 285

Glu Asp Gly Ser Tyr Phe Leu Tyr Ser Lys Leu Ser Val Asp Lys Ser
    290                 295                 300

Arg Trp Gln Arg Gly Asp Thr Phe Ile Cys Ala Val Met His Glu Ala
305                 310                 315                 320

Leu His Asn His Tyr Thr Gln Glu Ser Leu Ser His Ser Pro Gly Lys
                325                 330                 335

```
<210> SEQ ID NO 40
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cEl1 constant (canine) part of light chain

<400> SEQUENCE: 40

Leu Phe Gln Pro Ser Pro Asp Gln Leu His Thr Gly Ser Ala Ser Val
1               5                   10                  15

Val Cys Leu Leu Asn Ser Phe Tyr Pro Lys Asp Ile Asn Val Lys Trp
                20                  25                  30

Lys Val Asp Gly Val Ile Gln Asp Thr Gly Ile Gln Glu Ser Val Thr
            35                  40                  45

Glu Gln Asp Lys Asp Ser Thr Tyr Ser Leu Ser Ser Thr Leu Thr Met
        50                  55                  60

Ser Ser Thr Glu Tyr Leu Ser His Glu Leu Tyr Ser Cys Glu Ile Thr
65                  70                  75                  80

His Lys Ser Leu Pro Ser Thr Leu Ile Lys Ser Phe Gln Arg Ser Glu
                85                  90                  95

Cys Gln Arg Val Asp
            100
```